(12) United States Patent
Prusik

(10) Patent No.: US 6,924,148 B2
(45) Date of Patent: Aug. 2, 2005

(54) REACTIVITY CONTROL IN SUBSTITUTED DIACETYLENIC MONOMER SHELF LIFE MONITORING SYSTEMS

(75) Inventor: Thaddeus Prusik, Stroudsburg, PA (US)

(73) Assignee: TEMPTIME Corporation, Morris Plains, NJ (US)

( * ) Notice: Subject to any disclaimer, the term of this patent is extended or adjusted under 35 U.S.C. 154(b) by 125 days.

(21) Appl. No.: 10/611,302

(22) Filed: Jul. 2, 2003

(65) Prior Publication Data

US 2005/0003551 A1 Jan. 6, 2005

(51) Int. Cl.$^7$ .............................................. G01N 31/00
(52) U.S. Cl. ........................... 436/7; 374/102; 374/104; 374/106
(58) Field of Search ............................. 436/7; 422/56; 374/102, 104, 106

(56) References Cited

U.S. PATENT DOCUMENTS 4,208,186 A * 6/1980 Patel .............................. 436/2
4,228,126 A * 10/1980 Patel et al. .................... 422/56
4,276,190 A * 6/1981 Patel ......................... 252/408.1
4,298,348 A * 11/1981 Ivory ............................ 436/7

* cited by examiner

Primary Examiner—Yelena G. Gakh
(74) Attorney, Agent, or Firm—Kirkpatrick & Lockhart Nicholson Graham LLP; Anthony H. Handal (57) ABSTRACT

A product shelf life monitoring system comprising an active substituted diacetylenic monomer component indicator composition is responsive to an integral of varying temperature over time to effect a solid state polymerization in the active monomer which results in a visible change in color density or the like at a rate designed to closely approximate the degradation, or shelf life, of an associated foodstuff or medicament product. The reactivity of the monomer component upon which the time-temperature integral of the indicator composition, and thus the represented shelf life, primarily depends may be readily varied by refluxing a solution of the monomer in a selected solvent for a predetermined time prior to recrystallization of the monomer for incorporation into the indicator composition.

18 Claims, 5 Drawing Sheets

REACTIVITY CONTROL IN SUBSTITUTED DIACETYLENIC MONOMER SHELF LIFE MONITORING SYSTEMS

BACKGROUND OF THE INVENTION

The present invention relates to systems, and elements, components, and compositions therefor, for monitoring and indicating the elapse of a predetermined integral of ambient conditions, such as time, temperature, humidity, actinic radiation, vaporous atmosphere, and the like, to which such a system has been exposed. Typically, for example in monitoring the useful shelf life, i.e., the span of safe or potent utility, of a product of foodstuff, medicament, or the like which is known to be affected by a thermal ambient, an indicator system, often in the form of an affixed label, is associated with the product and exhibits a readily discernible property variation, such as a change of color or color density, upon the elapse of a given time-temperature integral representing the product's shelf life. To this end, the system comprises a composition appropriately formulated to provide such a color change response substantially concurrently with elapse of the given time-temperature integral and, thus, expiration of the predesignated shelf life.

In particular, the present invention relates to responsive compositions of shelf life monitoring systems comprising substituted diacetylenic monomer components which exhibit a distinct color change as a result of and generally concomitant with a solid state polymerization effected by the ambient condition integral; typically, as in the case of a time-temperature indicator (TTI) system, the integral of time and temperature. More particularly, through novel treatment of the active substituted diacetylenic monomer component incorporated into an indicator composition, the invention provides means for readily adjusting the reactivity of the indicator composition monomer in order to simply and economically achieve a monitoring system having the desired sensitivity and responsiveness within a target integral range indicative of the prescribed shelf life parameters of an associated product.

Substituted diacetylenic monomers useful in the present invention have been studied and utilized in shelf life monitoring systems for many years. Such utility of numerous monomers comprising at least two conjugated acetylene groups (—C≡C—C≡C—) and their unique physico-chemical properties, e.g., responsiveness to persistent temperature excursions by transforming into contrastingly colored solid state polymerization reaction products, have been described, for instance, by Patel et al. (U.S. Pat. No. 3,999,946). The synthesis of these monomers and their implementation in TTI and other shelf life indicator compositions are discussed there at length and continue to be useful in formulating embodiments of the present invention. Likewise, the use of these diacetylenic monomer shelf life system components and improvements thereon, including broad ranges of substituents and complexes, and improved methods of monomer synthesis and blending in co-crystallization operations, have been described further by Patel (U.S. Pat. Nos. 4,189,399 and 4,384,980) and Preziosi et al. (U.S. Pat. Nos. 4,789,637 and 4,788,151). Such useful descriptions and examples of these diacetylenic monomer components finding application in the present invention are incorporated herein by reference.

While the consistent responses of these diacetylenic monomer components to thermal stimuli, and the monitoring system compositions upon which they rely, provide a basis for numerous highly functional and reliable TTI system products, the shear number of time-temperature integral response ranges represented in the myriad diacetylenic monomer compounds available for these uses imposes practical and economical limitations on their overall utility. Although, as noted in the referenced descriptions, each basic monomer component synthesized under given conditions with given precursors and processing materials may be relied upon to exhibit substantially consistent TTI color density profiles, and thus provide reproducible indications of shelf life end points, market-place requirements for increasing numbers of varying shelf life ranges have led to the need for complete syntheses in each instance to yield monomers of matching response profiles. Such requirements for essentially ad hoc component synthesis have been practically alleviated only by an economically perverse inventorying of an endless number of narrow response range diacetylenic monomer components. There has thus resulted a need for a ready, reliable, and cost-effective means for varying the reactivity, and thus the TTI response ranges, of a few basic such monomer components in order to enable ready and economical formulation of TTI systems which are capable of representing a wider range in the burgeoning numbers of target products for which shelf life monitoring is a market-place necessity.

The present invention obviates the noted shortcomings and disadvantages of prior diacetylenic monomer composition TTI system products and provides such products which yield highly effective and improved ranges of reactivity and shelf life response while greatly reducing costs and achieving significant savings in system formulation time and material resources.

SUMMARY OF THE INVENTION

TTI systems of the instant genre generally comprise an active substituted diacetylenic monomer compound coating or ink composition which is associated with a target shelf life product, as on a container or label for the product. The active monomer component in such a system essentially represents the time-temperature shelf life integral of the associated product in that it is transformed in a solid state polymerization over the span of the selected integral to a reaction product of notably differing property, such as color or color density. As described in the referenced patent specifications, a monomer of desired shelf life time-temperature integral may be prepared by proper selection and balance of various parameters, such as precursor acetylenic condensate constituents or substituted variants thereof, conditions of synthesis and processing, solvents or procedures for crystallization, and matching of components for co-crystallized compositions.

In each instance of such syntheses, the derived active diacetylene monomer is a different compound reactive within a predetermined, yet narrowly limited, time-temperature integral range and effective in formulating only a single TTI indicator of similarly limited application. In order to shift the reactivity of such an indicator composition to achieve a higher, lower, or expanded integral range, re-synthesis or reformulation to obtain different active monomer compound components or intricate blending of a number of such different compounds has previously been required. Further, in order to be in the realm of reasonable practicality, any of these selected expedients has required individual stores of a number of precursors in intermediate stages of preparation. In view of the continuous state of reactivity of such materials, the maintenance of inventories requires special and costly storage facilities which afford appropriate control of temperature and other deleterious ambient conditions.

In contrast to these prior practices of extensive and intricate solution syntheses and blending of different diacetylenic monomer compounds, the present invention provides for accurately controlled extension or shifting of active TTI monomeric component reactivity by the simple treatment of a given monomer, or co-crystallized monomer composition. According to this invention, a ready and effective variation of monomer component reactivity is surprisingly achieved by heating and refluxing the monomer compound in a selected processing solvent prior to a crystallization or recrystallization operation in the synthesis of the compound. Unlike the prior synthesis and processing of candidate diacetylenic monomer compounds which were invariably carried out at temperatures meticulously maintained below the boiling point of the processing solvent and derived variant monomer compounds of different structure and consequent reactivity, the simple reflux treatment of the present invention is extraordinary in that, although providing active monomer components of demonstrably different TTI reactivity, such treatment causes no observable structural variation in the treated monomer compound component. Thus, the processing control accorded by the unique singular parameter variation of solution reflux time preceding a normal compound crystallization operation enables the invention to provide consistent and easily controlled reactivity variations in the resulting shelf life monitoring compositions.

In a representative embodiment of the present invention, a commonly employed TTI monomer component, for example, a 2,4-hexadiyn-1,6-bis(ethylurea) prepared from the reaction of mono-propargylamine and ethylisocyanate, was dissolved in glacial acetic acid and portions of the solution were heated to boiling (118° C.) and refluxed for varying times, up to about 15 minutes, prior to normal crystallization recovery in cold methanol with subsequent washing and drying. The resulting monomer products appeared, under microscopic; X-ray diffraction (XRD), and other analytical technique observations, to be substantially identical, yet when tested for thermal color-change response they exhibited, with increases in reflux time, increased reactivity to about four-fold in the 15 min sample.

As a result of this simple manner of shifting the representative shelf life end point of a single TTI monomer component, the present invention enables the use of a few well-tested substituted diacetylenic compounds of known and desirable properties to formulate TTI compositions of a wide range of target shelf lives without resort to the currently required individual synthesis and storage of a large number of different such compounds of lesser renown. Further, the breadth of reactivity and response range of a TTI composition may be readily varied by the simple blending of portions of a single given monomer compound which have been treated to varying degrees of reflux according to the invention. In this manner consistent composition properties of the single compound, such as solubility and particle morphology, as well as type of system response, e.g., end point color, may be maintained.

BRIEF DESCRIPTION OF THE DRAWING

The present invention will be described with reference to the accompanying drawing of which.

DESCRIPTION OF THE INVENTION

Figure 1:
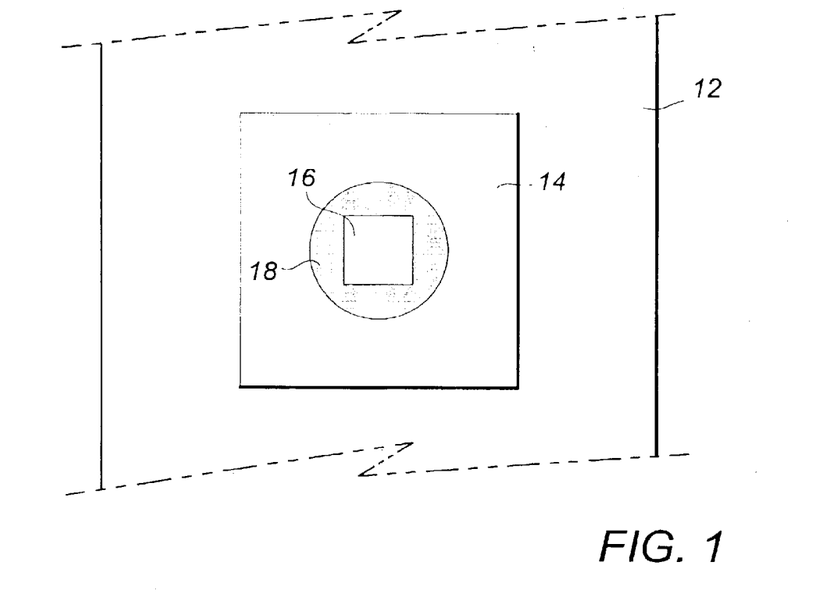
FIG. 1 depicts in plan view the representation of a time-temperature indicator (TTI) system label device typically comprising an active diacetylenic monomer indicator composition.

As seen in FIG. 1, a TTI system label utilized in association with a susceptible product 12 typically comprises a self-adhesive substrate 14 upon which is printed, coated, or otherwise deposited an area 16 of active diacetylenic monomer indicator composition. A threshold reference color body, such as shown in the form of a ring 18 surrounding area 16, is printed in close proximity to the active indicator composition and is provided in a color tone closely approximating the color density which will be developed in indicator area 16 upon accumulation of the time-temperature integral predetermined to be representative of the shelf-life beyond which the intended associated product, e.g., a foodstuff, such as fish or fowl, or a medicament, such as vaccine or medicine, is expected to lose its utility or potency. As an indication of such an expired shelf-life, the active composition area 16 of the label will notably change under the influence of ambient temperature beyond the threshold integral period to yield a tone which is at least as intense as that of reference color ring 18. The time-temperature integral period of a system composition is thus essentially dependent upon the reactivity of the active diacetylenic monomer component, i.e., the rate of color intensity development in the solid state polymerization reaction product of the monomer.

In the formulation of an appropriate active TTI composition, initial consideration centers upon the shelf life specification of the target susceptible product. That is to say, there are determined the maximum periods of time the target product may remain exposed to given temperature ambients before losing its safe utility or potency. When arranged for consideration, these data may typically be displayed as a trace 22, shown in FIG. 2, wherein the shelf life of the product varies inversely with the temperature ambient. Ideally, an active diacetylenic monomer component for a TTI composition would then be selected to match, in its reactivity, or rate of color developing polymerization, this product shelf life specification.

Figure 2:
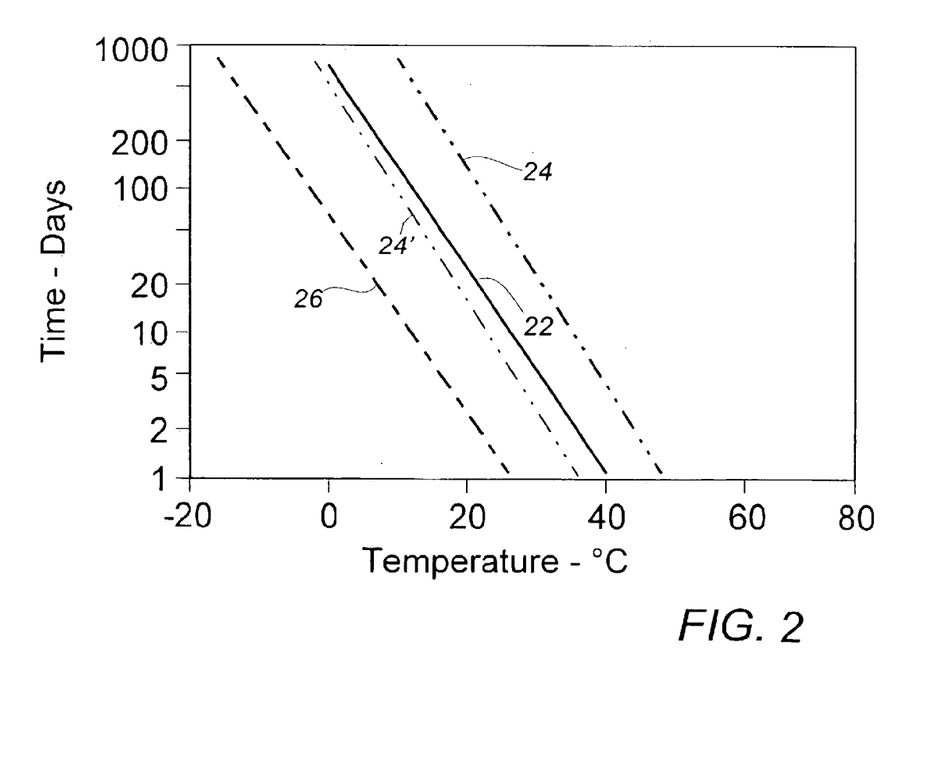
FIG. 2 presents graphic data depicting shelf life specification ranges of a selected susceptible product and TTI compositions of greater and lesser reactivity, including a variant according to the present invention.

Despite the extensive number of active diacetylenic monomer component compounds which may be available for such use, as evidenced by the referenced patent specifications, typically U.S. Pat. No. 3,999,946, U.S. Pat. No. 4,189,399, and U.S. Pat. No. 4,788,151, seldom does the reactivity of a single stock TTI composition monomer compound match an arbitrarily presented target product. Although an active monomer compound of closely approximating reactivity may ultimately be synthesized for use with a given product, substantial time and effort must normally be expended in numerous syntheses in order to obtain the practical candidate monomer, as well as to garner the relevant knowledge and experience of reactivity and the like essential for proper formulation and handling of a practical TTI material. Further, in many instances, the best approximation to an ideal monomer component for a given target product, considering economic, environmental, and like concerns, may exhibit a significantly greater reactivity, as of a hypothetical monomer at 26, or one which is lesser, as at 24, for which additional compensation efforts must be made.

Faced with these many fluctuating variables, one has thus far been forced to compromise among desired properties of practically available active diacetylenic monomer component compounds in order to more closely approximate the shelf life specification of the target product, usually through the blending of a number of monomer compounds exhibiting reactivities spanning that specification. As a result of the normally differing compound structures of such blended TTI composition monomer components, however, the introduction of undesirable composition properties and functional responses are not uncommon.

The method and resulting active TTI diacetylenic monomer composition components provided by the present invention obviate or alleviate many of the noted disadvantages of prior available practices, yet retain and enable continued use of those desirable component properties which have been proven over time. This end is achieved in the invention due to the fact that prior methods of synthesis, for example, and the wealth of experience previously gained in their use and the implementation of the resulting monomers continue for the most part to be applied. The invention, however, introduces, with exceptional results, a unique process step in the usual synthesis procedure and thereby produces monomer components of substantially invariant compound structure which nonetheless exhibit a wide and selectable range of polymerizing color development reactivity.

The improved process of the present invention may comprise, in an initial stage, the usual controlled sub-boiling temperature synthesis of the desired base diacetylenic monomer by means thoroughly described in the above-noted specifications. In lieu of contemporary synthesis of the monomer, stock compounds which have been previously so prepared and appropriately stored in inventory may be employed. In either event, the base monomer compound is dissolved in a selected solvent and the solution is heated to reflux temperature. The refluxing is continued for a prescribed period of time which may by simple testing be empirically determined relative to the desired monomer reactivity rate, whereupon the refluxing is terminated with cooling and crystallization of the monomer by any of the means noted in the previous specifications, e.g., by mixing the solution into a cold non-solvent such as methanol. Following purifying recrystallization and washing to a desired degree and drying, the treated monomer may be employed in the usual manner as the active component in a typical TTI ink or coating composition.

Such a simple reflux treatment of a base diacetylenic monomer in this manner results in a TTI composition active monomer component which surprisingly, while apparently retaining other significant properties of the untreated monomer compound, is shifted substantially in its polymerization reactivity from that of the latter. For a hypothetical monomer depicted in FIG. 2 as originally exhibiting a polymerization reactivity 24, the reflux treatment may be employed to effect an increase reactivity shift to a level indicated at 24' which will more closely approximate, or bracket with original reactivity 24 of the monomer, the shelf life specification 22 of the target product. Similarly, reflux treatment of a different diacetylenic monomer with an appropriate preselected solvent could be employed to decrease polymerization reactivity from a level 26 to more closely approximate the target shelf life specification.

Representative implementations of the present invention may be seen more specifically in the following examples.

EXAMPLE I

About 20 parts by weight of 2,4-hexadiyn-1,6-bis (ethylurea), a substituted diacetylenic monomer synthesized in a manner described in the note references and commonly used as the active component in TTI system indicator compositions, were dissolved in about 170 parts of glacial acetic acid and the solution was heated in a reflux flask apparatus to a temperature of 119° C. The heating was terminated, however, prior to the onset of solvent reflux and the solution was poured into about 200 parts of methanol held at about 5° C. in an ice bath and the mixture was cooled to about 10° C. to achieve substantially thorough recrystallization. The monomer crystal mass was then filtered from the fluid mixture, wash/filtered a number of times in cold methanol, and washed and dried from acetone under vacuum at room temperature. The recovered monomer sample was then held as a control for later testing.

EXAMPLE II

The procedure of Example I was repeated with the exception that the heated solution was refluxed at 119° C. for one minute prior to recrystallization in the cold methanol. The recovered sample was held for later testing.

EXAMPLE III

The procedure of Example I was repeated with the exception that the heated solution was refluxed at 119° C. for 5 min prior to recrystallization in the cold methanol. The recovered sample was held for later testing.

EXAMPLE IV

The procedure of Example I was repeated with the exception that the heated solution was refluxed at 119° C. for 15 min prior to recrystallization in the cold methanol. The recovered sample was held for later testing.

EXAMPLE V

Figure 3:
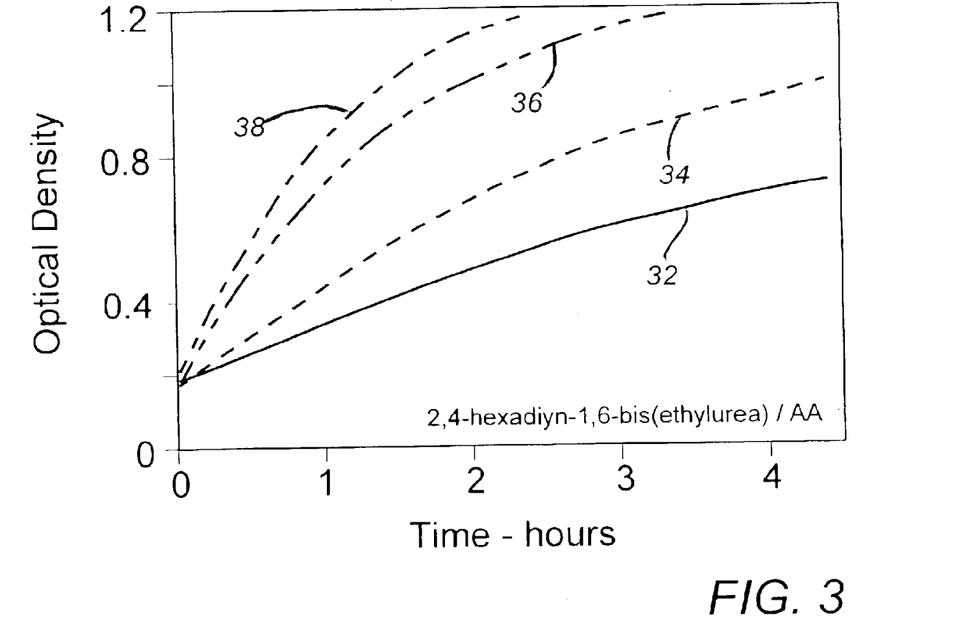
FIG. 3 presents graphic data depicting variations in reactivity of an active diacetylenic monomer indicator composition component as a result of implementation of the present invention.

Matching portions of each of the monomer samples prepared in Examples I–IV were held at a constant 70° C. in a testing arrangement and the optical densities of the color developing in the samples was measured at intervals with an X-Rite 404 Portable Reflectance Densitometer operating in the cyan mode. The respective color density data of these 2,4-hexadiyn-1,6-bis(ethylurea) samples, denoted "AA" to indicate reflux treatment in acetic acid, are shown in FIG. 3 where trace 32 depicts the comparative reactivity of the non-refluxed control sample of Ex. I, trace 34 depicts that of the one min treatment sample of Ex. II, trace 36 that of the 5 min treatment of Ex. III, and trace 38 that of the 15 min treatment of Ex. IV. As is apparent, the reactivity of this monomer increases with the length of reflux treatment in acetic acid, at least up to 15 min.

Figure 5:
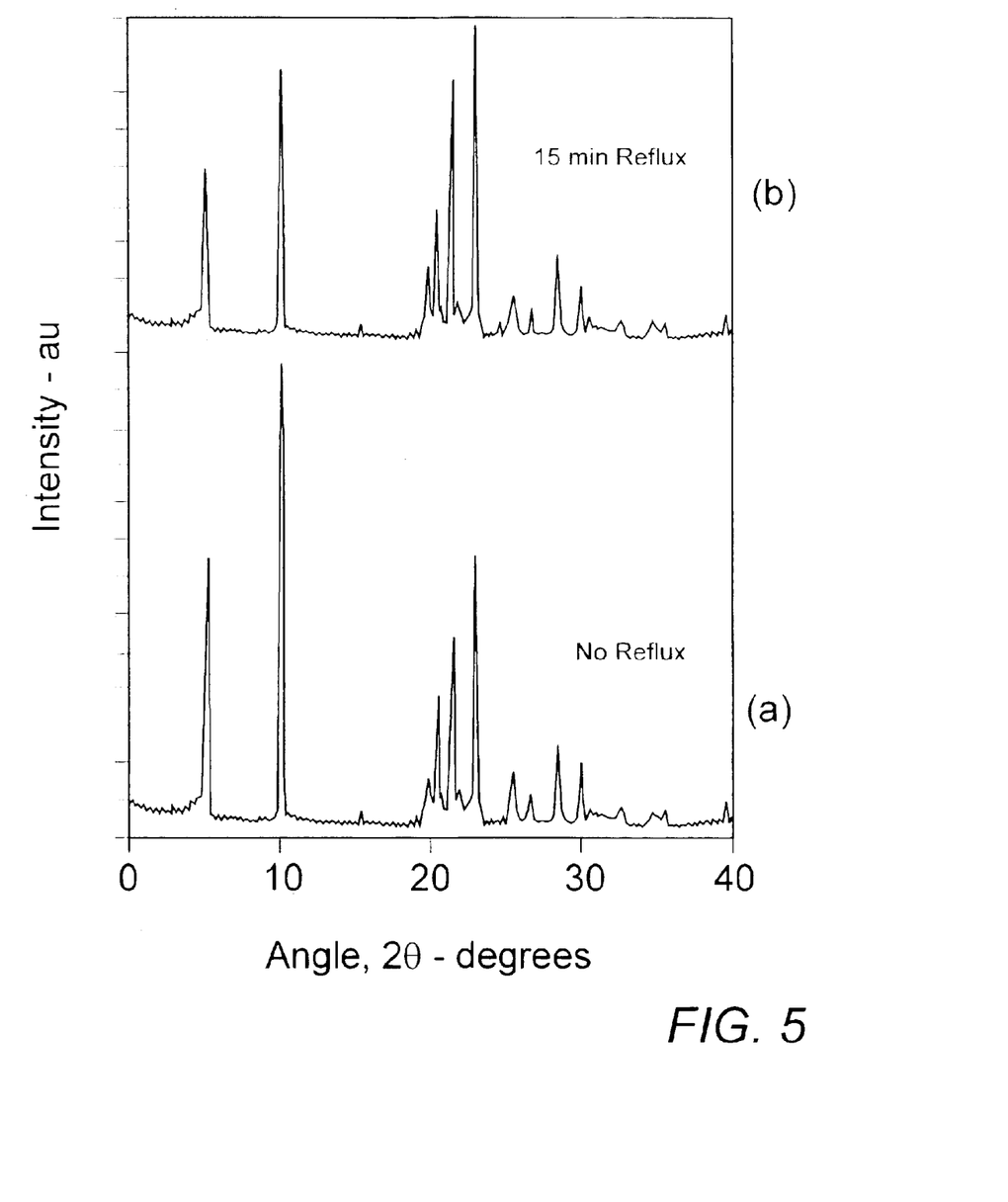
FIG. 5 presents comparative graphic XRD data confirming the negligible effect of implementation of the present invention upon the structure of a diacetylenic monomer compound.

Of particular note with respect to the progressive increase of reactivity in the samples of Examples I–IV is the fact that whereas previous studies of varying reactivities resulting from synthesis of substituted diacetylenic monomer compounds have regularly observed a change in compound formation, e.g., the crystal structure, with changes in reactivity, both slower and more rapid, resulting from variations in synthesis procedures and the like, the monomers treated according to the present invention remain substantially identical in structure despite demonstrated significant changes in their reactivity. Such surprising identity among monomer materials of varying reactivity, as confirmed by the identical definitive Bragg peak positions in the comparative FIGS. 5(*a*) and 5(*b*) X-ray diffraction data traces of Example I and IV samples, provides the unparalleled advantage of enabling consistent and reliable adjustment of an ultimate TTI system shelf life monitoring composition by means of simple monomer component blending without concern for compound incompatibilities.

EXAMPLE VI

Figure 4:
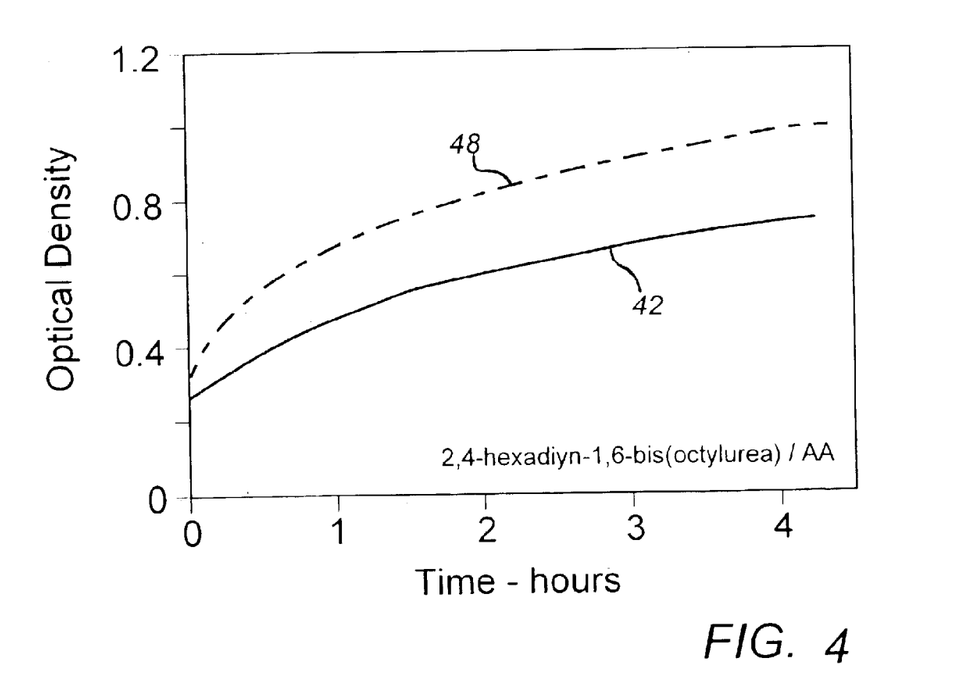
FIG. 4 presents graphic data depicting variations in reactivity of another active diacetylenic monomer indicator composition component as a result of implementation of the present invention.

The procedures of Examples I and IV were repeated with similar amounts of 2,4-hexadiyn-1,6-bis(octylurea) in acetic acid. The respective test data of the resulting materials are depicted in FIG. 4 where the reactivity of the monomer after 15 min reflux treatment, as shown at trace 48, increased substantially from the non-refluxed control sample of trace 42.

EXAMPLE VII

Figure 6:
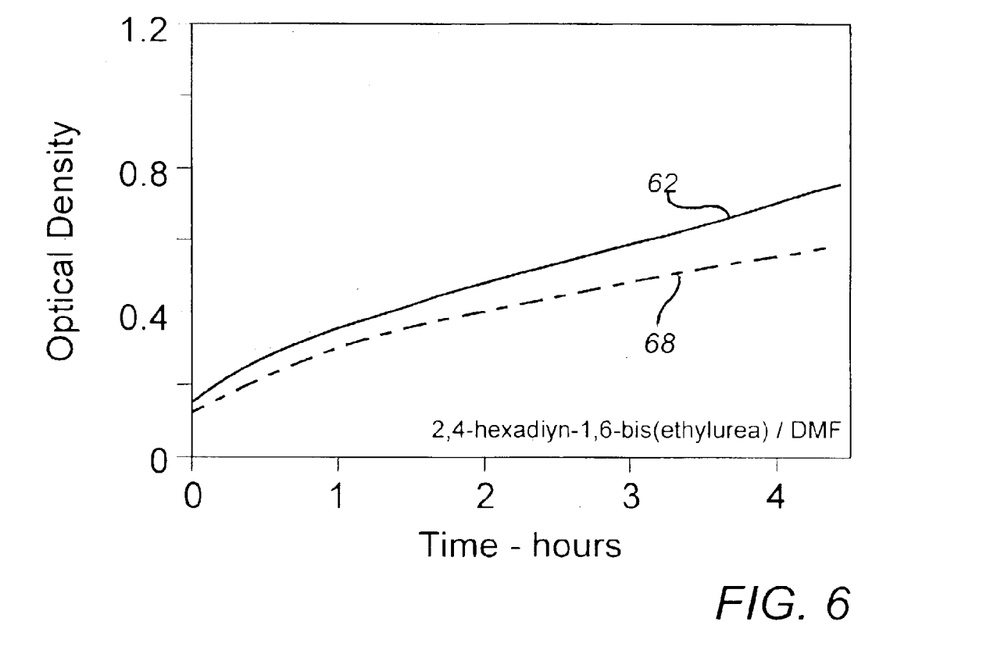
FIG. 6 presents graphic data depicting variations in reactivity of the active diacetylenic monomer indicator composition component of FIG. 3 as a result of implementation of a variant embodiment of the present invention.

The procedures of Examples I and IV were repeated with similar amounts of 2,4-hexadiyn-1,6-bis(ethylurea); however, reflux treatment of the monomer was carried out in dimethyl formamide (DMF) solvent at its reflux temperature of 153° C. The respective test data of the resulting samples are depicted in FIG. 6 where the reactivity of the monomer after 15 min reflux treatment, as shown at trace 68, decreased significantly from the non-refluxed control sample of trace 62. These results demonstrate the flexibility of the invention in providing, through a simple variation in processing solvent, a shift of reactivity in a single given active TTI diacetylenic monomer component to either an increase or decrease in order to more closely approximate the shelf life specification of a target associated product.

EXAMPLE VIII

Figure 7:
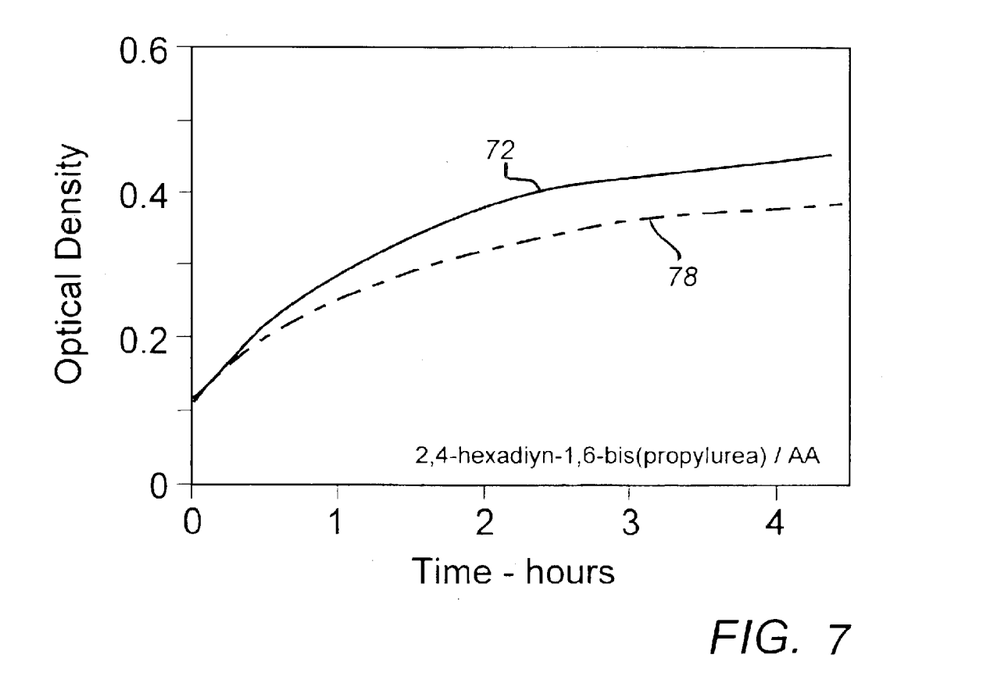
FIG. 7 presents graphic data depicting variations in reactivity of yet another active diacetylenic monomer indicator composition component as a result of implementation of the present invention.

A similar decrease in reactivity was observed in the reflux treatment of 2,4-hexadiyn-1,6-bis(propylurea) in acetic acid where the procedures of Example VII were repeated with these materials. The test data depicted in FIG. 7 show the decrease in reactivity from that of the non-refluxed sample trace 72 to that of the 15 min reflux of trace 78.

EXAMPLE IX

Figure 8:
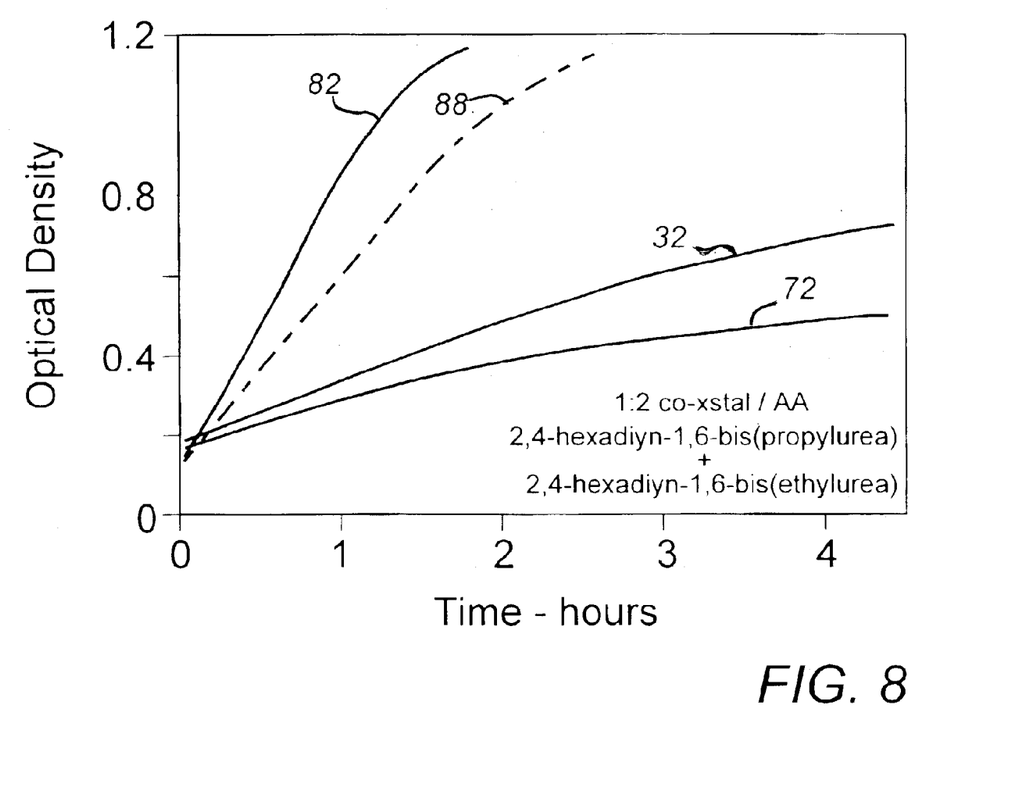
FIG. 8 presents graphic data depicting variations in reactivity of a further active diacetylenic monomer indicator composition component as a result of implementation of the present invention

The advantages of co-crystallization in the preparation of active TTI diacetylenic monomer components, as described, for example, in U.S. Pat. No. 4,788,151, may be enjoyed as well in the present invention. This result was confirmed by repeat of the procedures of Examples I and IV with a mixture of about 13.4 parts of 2,4-hexadiyn-1,6-bis(ethylurea) and 6.7 parts of 2,4-hexadiyn-1,6-bis(propylurea) in acetic acid. The respective test data of the resulting co-crystallized monomer components are depicted in FIG. 8 where the reactivity of the sample subjected to 15 min reflux treatment, as shown at trace 88, was decreased significantly from that of the non-refluxed control sample of trace 82. The data traces of non-refluxed control samples 32 and 72 of individual 2,4-hexadiyn-1,6-bis(ethylurea) and 2,4-hexadiyn-1, 6-bis(propylurea) monomers are also shown as evidence of the retained effect of the co-crystallization procedures.

Numerous other active TTI system diacetylenic monomer components of selectively varied reactivity may be prepared according to the present invention utilizing the many monomer compounds and recrystallization solvents described in the above-noted patent specifications. In each instance, the range of time-temperature integral endpoints achieved according to the invention to now more closely represent target foodstuff and medicament shelf lives may be reached over reflux periods of up to about 45 min as may readily be determined by simple and routine test methods without resort to extensive laboratory investigation or inventive measures. The ultimate utilization of these select monomer components in TTI compositions may, likewise, follow any of the previously preferred practices including incorporation into printing inks or coating lacquers for application to labels or packaging materials for target shelf life products.

It is anticipated that other embodiments and variations of the present invention will become readily apparent to the skilled artisan in the light of the foregoing description and examples, and such embodiments and variations are intended to likewise be included within the scope of the invention as set out in the appended claims.

What is claimed is:

1. The method of varying the heat-induced solid state polymerization reactivity of a distinctively crystalline structured substituted diacetylenic monomer shelf life monitoring system composition, which method comprises:
   a) providing a solution of said monomer component of a, in a first state of said reactivity at a temperature below the reflux temperature of said solution,
   b) heating said solution to said reflux temperature in a reflux system,
   c) continuing reflux of said solution for a predetermined time period, and
   d) recrystallizing the solute from said refluxed solution to thereby yield said monomer component in a second state of said reactivity while having substantially retained said crystalline structure.

2. The method according to claim 1 wherein said reflux period extends up to about 45 minutes.

3. The method according to claim 1 wherein the solvent of said solution is selected from the group consisting of acetic acid and dimethyl formamide.

4. The method according to claim 3 wherein said reflux period extends from about one to 15 minutes.

5. The method according to claim 1 wherein said monomer component is selected from the group consisting of 2,4-hexadiyn-1,6-bis(alkylurea) compounds and co-crystallized combinations thereof.

6. The method according to claim 5 wherein said monomer component is selected from the group consisting of ethyl-, propyl-, and octyl-substituted 2,4-hexadiyn-1,6-bis (alkylurea) compounds and co-crystallized combinations thereof.

7. A product shelf life monitoring system composition comprising an active substituted diacetylenic monomer component derived by recrystallization from a refluxed solution of said component according to the method of claim 1.

8. A composition according to claim 7 wherein the monomer component of said refluxed solution is selected from the group consisting of 2,4-hexadiyn-1,6-bis(alkylurea) compounds and co-crystallized combinations thereof.

9. A composition according to claim 8 wherein the monomer component of said refluxed solution is selected from the group consisting of ethyl-, propyl-, and octyl-substituted 2,4-hexadiyn-1,6-bis(alkylurea) compounds and co-crystallized combinations thereof.

10. A composition according to claim 7 wherein the solvent of said solution is selected from the group consisting of acetic acid and dimethyl formamide.

11. A composition according to claim 10 wherein the period of reflux of said component solution extends from about one to 15 minutes.

12. A product shelf life monitoring system comprising a substrate surface bearing an active indicator composition responsive in a visible change under incident thermal energy to which an associated product is susceptible, said indicator composition comprising an active substituted diacetylenic monomer component derived by recrystallization from a refluxed solution of said component according to the method of claim 1.

13. A system according to claim 12 wherein said associated product is a foodstuff.

14. A system according to claim 12 wherein said associated product is a medicament.

15. A system according to claim 12 wherein the monomer component of said refluxed solution is selected from the group consisting of 2,4-hexadiyn-1,6-bis(alkylurea) compounds and co-crystallized combinations thereof.

16. A system according to claim 12 wherein the monomer component of said refluxed solution is selected from the group consisting of ethyl-, propyl-, and octyl-substituted 2,4-hexadiyn-1,6-bis(alkylurea) compounds and co-crystallized combinations thereof.

17. A system according to claim 16 wherein the solvent of said solution is selected from the group consisting of acetic acid and dimethyl formamide.

18. A system according to claim 17 wherein the period of reflux of said component solution extends from about one to 15 minutes.

* * * * *